United States Patent [19]
Heitmann et al.

[11] Patent Number: 5,676,546
[45] Date of Patent: Oct. 14, 1997

[54] DENTAL APPLIANCE

[76] Inventors: Scott L. Heitmann, Whitehall Rd, Glen Devin Condominiums #45, Amesbury, Mass. 01913; Daniel E. Brayton, 36 Front St., Marblehead, Mass. 01945

[21] Appl. No.: 774,628

[22] Filed: Dec. 30, 1996

[51] Int. Cl.$^6$ .................................................. A61C 13/00
[52] U.S. Cl. ................................. 433/199.1; 433/191
[58] Field of Search ........................ 433/199.1, 167, 433/213, 214, 191

[56] References Cited

U.S. PATENT DOCUMENTS

| | | | |
|---|---|---|---|
| 108,588 | 10/1870 | Hale | 433/191 |
| 606,198 | 6/1898 | Evans | 433/199.1 |
| 1,750,810 | 3/1930 | Miller | 433/213 |
| 1,784,250 | 12/1930 | Noyes | 433/199.1 |
| 1,899,521 | 2/1933 | Nudell | 433/199.1 |
| 1,945,767 | 2/1934 | Bergerhausen | 433/199.1 |
| 2,418,833 | 4/1947 | Harris et al. | 433/199.1 |
| 3,423,830 | 1/1969 | Halpern et al. | 433/199.1 |
| 4,024,637 | 5/1977 | Colpitts | 433/199.1 |
| 4,094,067 | 6/1978 | Hazar | 433/213 |
| 4,267,133 | 5/1981 | Kohmura et al. | 433/195 |
| 4,376,629 | 3/1983 | Eberling | 433/199.1 |
| 4,388,069 | 6/1983 | Orlowski | 433/199.1 |
| 4,721,466 | 1/1988 | Thalheimer | 433/199.1 |
| 5,304,062 | 4/1994 | Saitoh et al. | 433/191 |
| 5,403,186 | 4/1995 | Ginsburg | 433/199.1 |

FOREIGN PATENT DOCUMENTS

| | | | |
|---|---|---|---|
| 3742640 | 12/1987 | Germany. | |
| 3811645 | 4/1988 | Germany. | |
| 301459 | 6/1989 | Japan | 433/199.1 |
| 1456135 | 2/1989 | U.S.S.R. . | |

*Primary Examiner*—John J. Wilson
*Attorney, Agent, or Firm*—Michael A. Centanni

[57] ABSTRACT

Partial and full prosthetic denture plates and processes to make them are disclosed. A partial denture plate comprised of a denture base formed of a composite laminate having an intermediate layer of a woven fabric with non-woven veils disposed on opposite sides thereof is encapsulated in a polymeric resin. The denture base is molded to conform to a shape of a patient's mouth. The denture base has at least one tab extending from the denture base. The tab is oriented to be in alignment with the patient's natural teeth. A synthetic tooth is molded on each tab resulting in a denture device having a fiber-reinforced composite base and a synthetic tooth, or teeth, molded on each tab, the tab or tabs made of and extending from the fiber-reinforced composite. Similarly, a full denture plate is disclosed. A rib is positioned on a parabolic strip of the composite laminate, the rib generally conforming to a patient's gum line. Artificial teeth are then molded on the rib resulting in a full, prosthetic, denture plate.

33 Claims, 4 Drawing Sheets

DENTAL APPLIANCE

FIELD OF THE INVENTION

The present invention relates generally to dental appliances, and more particularly to dentures and a method of making same.

BACKGROUND OF THE INVENTION

Conventional prosthetic denture devices have a denture base formed of a resin and/or metallic material. An artificial tooth, or a set of teeth, is set into the resin material which is subsequently cured and hardened. Specifically, the root of each tooth is imbedded in and adhered to the resin material that forms the denture base.

A problem with such denture devices is that during use the artificial teeth do not feel as sturdy or as anchored as normal teeth. Further, severe use may dislodge a tooth or teeth from the denture base. With metal type bases, the weight causes the base to fall off the mouth roof easier. In addition, resin plates are weak and metals costly.

The present invention overcomes these and other problems and provides a prosthetic denture device wherein a portion of the denture base extends into and is embedded in each artificial tooth.

SUMMARY OF THE INVENTION

In accordance with the present invention, there is provided a prosthetic denture device comprised of a prepreg dental base vacuum/pressure formed to conform to the interior surface of a patient's mouth. The dental base is formed of resin impregnated, reinforced layers of fabric. At least one tab extends from the denture base. The tab is oriented along a tooth axis relative to the denture base. An artificial tooth is formed on the tab to be in alignment with the natural position of the permanent teeth in a patient's mouth.

In accordance with another aspect of the present invention, there is provided a denture plate comprised of a denture base. The denture base is formed of a composite laminate having an intermediate layer of a woven fabric or a cross-plied, unidirectional material and having non-woven veils disposed on each side of the woven, intermediate layer. The intermediate layer of woven fabric and the non-woven veils are encapsulated in a cured, polymeric resin. At least one tab extends from the denture base. The tab is oriented to be aligned with the orientation of the natural teeth of a patient's mouth. A synthetic tooth is molded on the tab, or tabs, completing the denture plate.

In accordance with another aspect of the present invention, there is provided a method of forming a prosthetic denture device, comprising the steps of:

a) creating a cast of a patient's mouth, having the patient's palate and teeth formed thereon;

b) placing a prepreg laminate material onto the cast, the laminate sheet being shaped to generally conform and match the inner profile of the tooth line and to include tabs at locations of missing teeth, the tabs oriented to be in alignment with the teeth of the cast;

c) vacuum or pressure drawing the laminate onto the cast until the laminate conforms to the shape of the palate;

d) additional pressure is then applied to densify the reinforcing layers, remove excess resin and normalize cross sectional thickness;

e) curing said vacuum-drawn laminate sheet to form a rigid dental plate conforming to the palate of the patient's mouth, wherein each of the tabs is oriented along a normal axis of the patient's teeth; and f) molding or bonding an artificial tooth onto each tab.

It is an object of the present invention to provide an improved prosthetic denture device.

It is another object of the present invention is to provide a prosthetic denture device as described above wherein each artificial tooth is formed around, and is bonded to, a portion of the denture base.

Another object of the present invention is to provide a prosthetic denture device as described above wherein a portion of the dental base forms the core of the artificial tooth.

A still further object of the present invention is to provide a prosthetic denture device as described above wherein each artificial tooth is mounted to a tab or a ridge which forms a portion of the dental base.

Another object of the present invention is to provide a prosthetic denture device as described above wherein the dental base is formed of multiple layers of thin, fiber reinforced, polymeric laminates.

A still further object of the present invention is to provide a prosthetic denture device as described above wherein the reinforcing fibers are synthetic fibers.

A still further object of the present invention is to provide a prosthetic denture device as described above wherein the fiber reinforcement takes the shape of woven fabric, unidirectional fabric, non-woven veils or a combination thereof.

A still further object of the present invention is to provide a prosthetic denture device formed of a thermoplastic or a thermoset resin and a fiber/veil combination that generates a final laminate having a tensile modulus of at least about 0.75 million PSI.

A still further object of the present invention is to provide a prosthetic denture device as described above wherein a biocompatible, thermosetting or thermoplastic resin forms the denture base.

A still further object of the present invention is to provide a prosthetic denture device as described above wherein the denture base is formed of a preferably biocompatible material such as an acrylic based polymer.

These and other objects of the invention will become apparent to those skilled in the art upon a reading and understanding of the specification together with the attached drawings.

DETAILED DESCRIPTION OF PREFERRED EMBODIMENT

Figure 1:
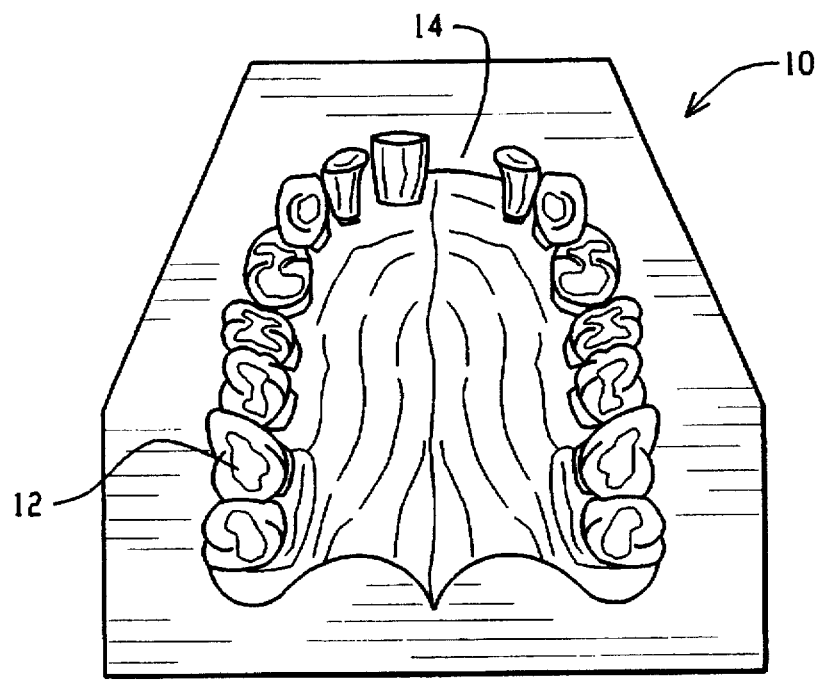
FIG. 1 is a planned view of a plaster cast of an upper denture of a patient's mouth, showing a missing tooth.

Referring now to the drawings wherein the purpose is for illustrating a preferred embodiment of the invention only and not for the purpose of limiting same, FIG. 1 shows a cast 10 having an impression of an upper denture 12 of a patient's mouth formed thereon.

According to the present invention, the cast 10 of the patient's mouth is formed by conventional means using an elastomeric material. This elastomeric material is used to form a mold (not shown) conforming with the teeth profile and gum line of a patient's mouth. Using the elastomeric mold, plaster cast 10 of the patient's mouth is formed to provide a denture profile as shown in FIG. 1. The method of forming plaster cast 10 of the patient's mouth heretofore described is conventionally known and in and of itself forms no part of the present invention. As is conventionally known, a cast 10 formed according to the above procedure reproduces with great accuracy the inner contours of the patient's mouth and shows as voids locations of missing teeth. Specifically, the plaster cast establishes the contours of a patient's palate and teeth line. In the embodiment shown, a gap 14 exists in the denture 12 showing where the patient is missing a tooth.

Figure 4:
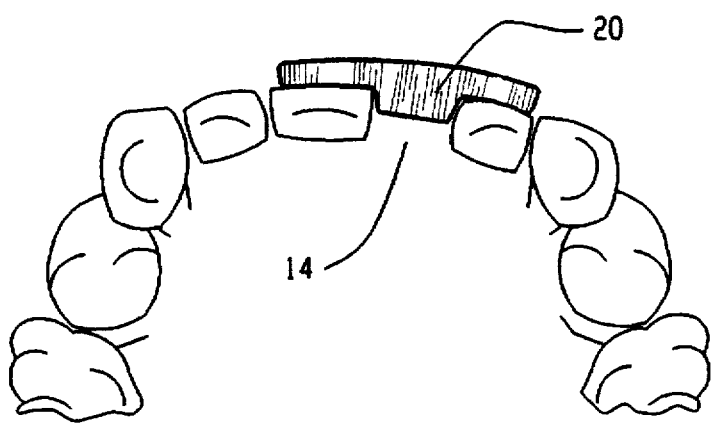
FIG. 4 is an enlarged view of a portion of the dental mold shown in FIG. 1 showing a tab locator molded, positioned and cured thereon.

According to the present invention, a wall or barrier element 20 is formed across the gap 14 created by a missing tooth, as shown in FIG. 4. Wall element 20 may be formed of various materials, but in the embodiment shown is formed of a light cured, resin material.

Figure 2:
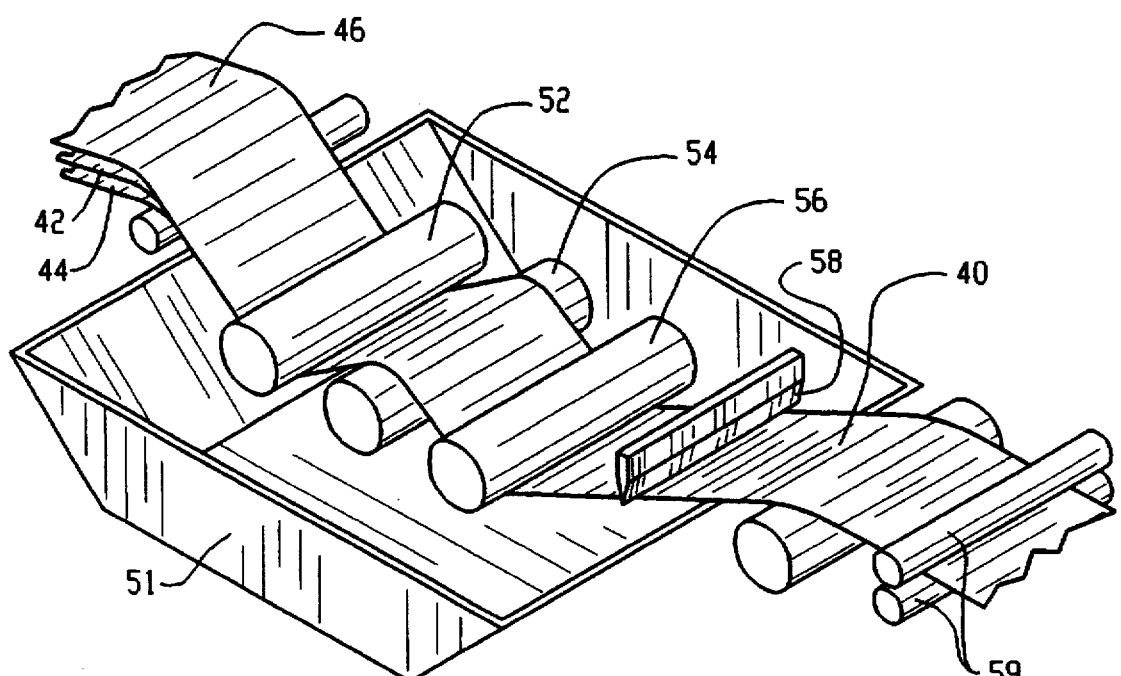
FIG. 2 is a schematic representation of a method of forming a laminate material used in forming a prosthetic denture device according to the present invention.

Referring now to FIG. 2, a method of forming a material for use as a denture base is schematically shown. According to the present invention, a denture base 30 is formed of a prepreg material designated 40 in the drawings. In the embodiment shown, prepreg material 40 is formed of an inner layer 42 of a fabric material, preferably woven, or preferably cross-plied, unidirectional materials disposed between layers 44, 46 of a non-woven, fiber veil. Veils 44, 46 create a sandwich structure that enhances the overall stiffness of prepreg 40 in the cured configuration. In the embodiment shown, a material woven of polyethylene fibers manufactured by Fabric Development called Spectra®, style 714 fabric (dense square weave), forms inner layer 42. Layer 42 may also be formed of other synthetic, thermoplastic fibers such as polyester. An acrylic, non-woven, fabric material forms veils 44, 46. Veils 44, 46 are preferably fine smooth sheets to provide smooth outer surfaces to denture base 30 (denture base 30 shown in cross-section in a patient's mouth in FIG. 6) as will be understood from a further reading of the specification. A suitable veil material, manufactured by Freudenburg, is Pellon® 1772, a polymethylmethacrylate veil having a thickness of about 0.0085 inches. The fiber, non-woven veils 44, 46 are secured to layer 42 by means of a resin material. Veils 44, 46 and layer 42 are preferably passed through a tank, designated 51 in FIG. 2, containing the resin material (not shown). An acrylic, light-curable resin, such as BIS-GMA, a polymeric material commonly used in the dental industry, is preferably used to secure layer 42 and veils 44, 46, and to provide the encapsulating material of prepreg 40. The resin is preferably heated and forced into layer 42 and veils 44, 46 by means of a plurality of rollers 52, 54 and 56 as schematically illustrated in FIG. 2. The rolling technique forces the resin thoroughly around the respective fibers, forming the woven fabric of inner layer 42 and non-woven veils 44, 46. Excessive resin may be removed from layer 42 and veils 44, 46 by a wiper blade 58 and squeeze rollers 59. Thus, as illustrated in FIG. 2, the resin material may be impregnated onto layer 42, veils 44, 46 by means of a resin bath with rollers 52, 54 and 56 forcing the resin into same, and wiper blade 58 and squeeze rollers 59 forcing out excess non-functional resin.

Inner layer 42 and veils 44, 46 basically provide reinforced fibers for the resin matrix. In one embodiment of the present invention, prepreg 40 is preferably formed of about 50% (fifty percent) to about 70% (seventy percent) reinforcement fibers, e.g., woven fabric and non-woven veils, and about 50% (fifty percent) to about 30% (thirty percent) resin by weight. More preferably, prepreg 40 is formed of about 55% (fifty-five percent) to about 65% (sixty-five percent) reinforcement fibers, e.g., woven fabric and non-woven veils, and about 45% (forty-five percent) to about 35% (thirty-five percent) resin by weight. Most preferably, prepreg 40 is formed of about 60% (sixty percent) reinforcement fibers, e.g., woven fabric and non-woven veils, and about 40% (forty percent) resin by weight. In a preferred embodiment of the present invention, release films (not shown) may be placed over non-woven veils 44, 46 to allow handling of prepreg 40.

Figure 3:
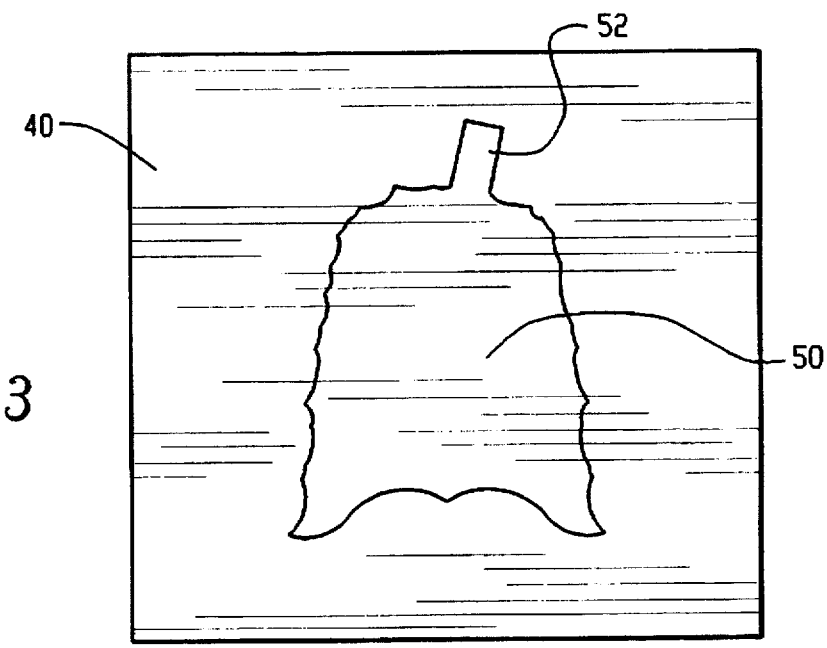
FIG. 3 is a view of a laminate material formed according to the process shown in FIG. 2 having a dental plate pattern outlined thereon.
Figure 5:
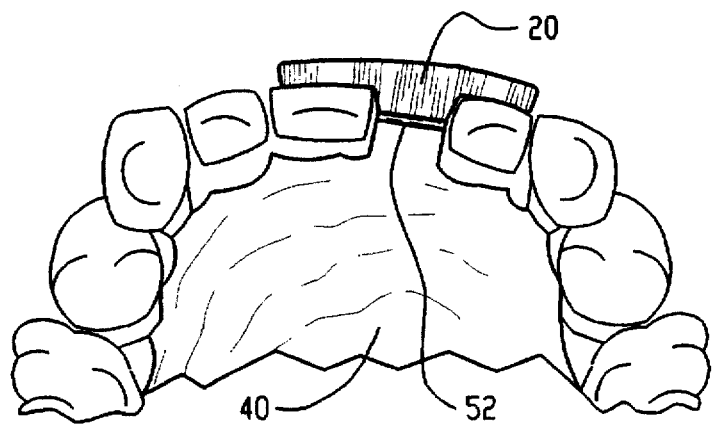
FIG. 5 is a view of the cast shown in FIG. 1 having the dental base pattern positioned thereon with a tooth mounting tab positioned against the tab locator.

Referring now to FIG. 3, a piece of prepreg 40 sufficient to cover cast 10 is removed from the laminate sheet and is forced onto cast 10 so as to roughly approximate the contour of the patient's palate. Prepreg 40 is marked to find the outline of the patient's tooth line to indicate where gap 14 exists corresponding to the patient's missing tooth. FIG. 3 shows a pattern 50 defined by the outline of the palate and tooth line. Pattern 50 includes a tab 52 located at gap 14. According to the present invention, the pliable prepreg 40 is cut along the outline of pattern 50 to closely approximate the palate and gum line of the patient. Prepreg 40 is positioned on plaster cast 10 with tab 52 positioned within gap 14 formed by the missing tooth, as shown in FIG. 5. In this respect, tab 52 is positioned against the reinforcing barrier element 20. Cast 10 with pattern 50 thereon is placed within a conventionally known vacuum chamber. A vacuum is drawn on plaster cast 10 and prepreg 40 to draw prepreg 40 into conformity with plaster cast 10. Additional pressure up to 100 psi is applied using a standard, dental autoclave. In other words, prepreg 40 conforms to and molds with the profile of the patient's mouth as established by plaster cast 10. A light source is applied above the assembly to partially cure prepreg 40. Partially cured pattern 50, which has now conformed to the patient's mouth, is carefully removed from plaster cast 10. Prepreg 40 is now completely cured by means of a light source. When further cured, prepreg 40 is rigid and conforms to the palate of the patient's mouth and has tab 52, in the case of an upper denture, extending downward therefrom. Tab 52 is positioned to be in alignment with the tooth line of the patient's upper dentures. When fully cured, prepreg 40 may be machined and polished by conventional means to remove excess material and rough areas so as to comfortably be positioned within the patient's mouth. Prepreg 40, when fully cured in a shape conforming to the patient's mouth, defines denture base 30 (shown in cross-section in FIG. 6).

The thickness of denture base 30 is basically controlled by the thickness of layers 42, 44, 46 and resin content. As will be appreciated, by forming denture base 30 from a resin reinforced by layers 42, 44 and 46, thin denture devices may be made. Denture base 30 having a thickness of about 0.060" or less may be made. In addition, employing the processes and materials disclosed in the present invention allows for the production of denture plates of specific thicknesses to within tolerances of ±0.010". A thin, strong, uniform, light-weight and comfortable denture base can be fabricated quickly in a one-sided tool.

Figure 6:
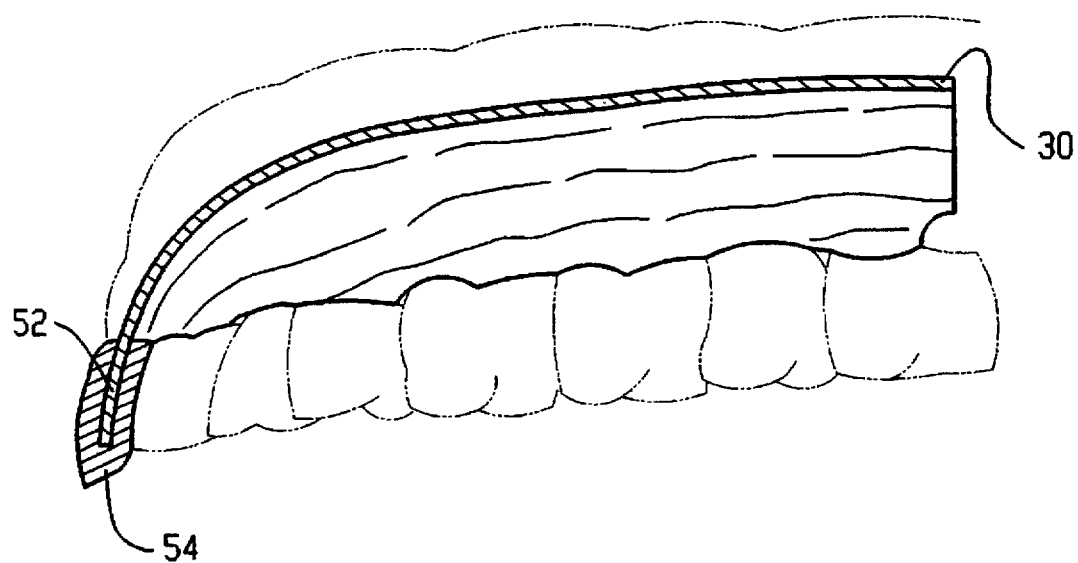
FIG. 6 is a cross-sectional view of a prosthetic denture device, according to the present invention, having an artificial tooth formed thereon.

With denture base 30 fitted and conforming to the patient's mouth, an artificial tooth 54 is molded, bonded or otherwise formed on tab 52, as best seen in FIG. 6. Artificial tooth 54 may be formed of a cap-type material or may be molded with a light-curable, ceramic material. The forming of tooth 54 may be done in a laboratory setting but is preferably done with denture base 30 in the patient's mouth.

In the present invention, various polymeric materials may be used as an encapsulating resin. For example, thermoplastic, thermosetting or a combination of both may be used as an encapsulating resin. In addition, any process, material design or system that encompasses thermoset and/ or thermoplastic matrices and a fiber/veil combination that generate a final prepreg 40 having a cured laminate, tensile modulus of at least about 0.75 million PSI may be used.

Importantly, the fibers of inner layer 42 that are located within the tooth are continuous into denture base 30. As a result, it is believed that loads placed on tooth 54 are distributed throughout denture base 30. It is further believed that the fiber loading increases shear properties at the interface of tooth 54 and denture base 30, providing improved bending moment characteristics when tooth 54 and denture base 30 are placed under a load.

The chemical bond line of the tab on the denture device is perpendicular to the shear plane. It is believed that this establishes a compressive load in the bond line that improves load handling capabilities.

The present invention thus provides a prosthetic denture device wherein a portion of the denture base 30 extends and projects into artificial tooth 54 to form a more rigid, solid and lifelike mounting.

A partial denture having excellent physical properties and a comfortable fit is made in accordance with the following EXAMPLE.

EXAMPLE

BIS-GMA, polymeric resin is heated to 200 degrees Fahrenheit to drop its viscosity so as to enhance its penetration around individual Spectra® fibers of style 714 fabric (dense square weave). Veils 44, 46 are made of layers of Pellon® 1772 polymethylmethacrylate, each layer having a thickness of about 0.0085 inches. Two veils, 44 and 46, are placed on opposite sides of the Spectra® fabric 42.

At first, as seen in FIG. 2, Spectra® fabric 42, impregnated with resin, is placed between release plies and squeezed between rollers 52, 54; rollers 52, 54 are preferably hard and are preferably made of ceramic-based materials. The first layer of Pellon® 44 is then placed on top of the resin impregnated Spectra® 42, the two layers are then placed in between release plies and squeezed in between rollers 52, 54. The third layer of Pellon® 46 is then placed on the other side of Spectra® fabric 42, the three layers are placed in between release layers and are squeezed between rollers 52, 54 producing prepreg 40.

A denture base 30, with tab 52 extending therefrom, is made as described hereinabove. The fiber orientation of the Spectra® fabric is zero (0) degrees on axis to tooth centerline. Cast 10 and pattern 50 are placed in a vacuum/pressure of 14.8 psi/60 psi under white light to partially cure prepreg 40. The final cure of the molded prepreg 40 is done in a Triad unit for about 5 (five) to 10 (ten) minutes. Any Spectra® filaments protruding from the finally cured denture base 30 or tab 52 are flashed off with a flame that melts the filaments away. Finally, each artificial, synthetic tooth 54 is fitted on each tab 52 for bond and fit of the patient's bite.

The denture and procedure heretofore described are related to a partial denture.

Figure 7:
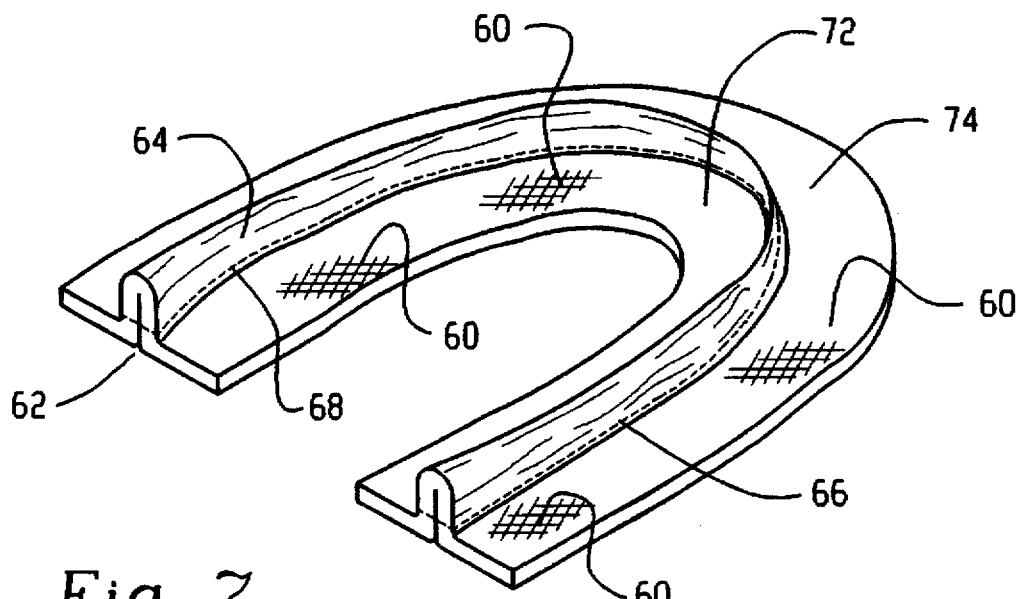
FIG. 7 is a perspective view of a laminate material having the denture base for a full denture pattern outlined thereon.
Figure 8:
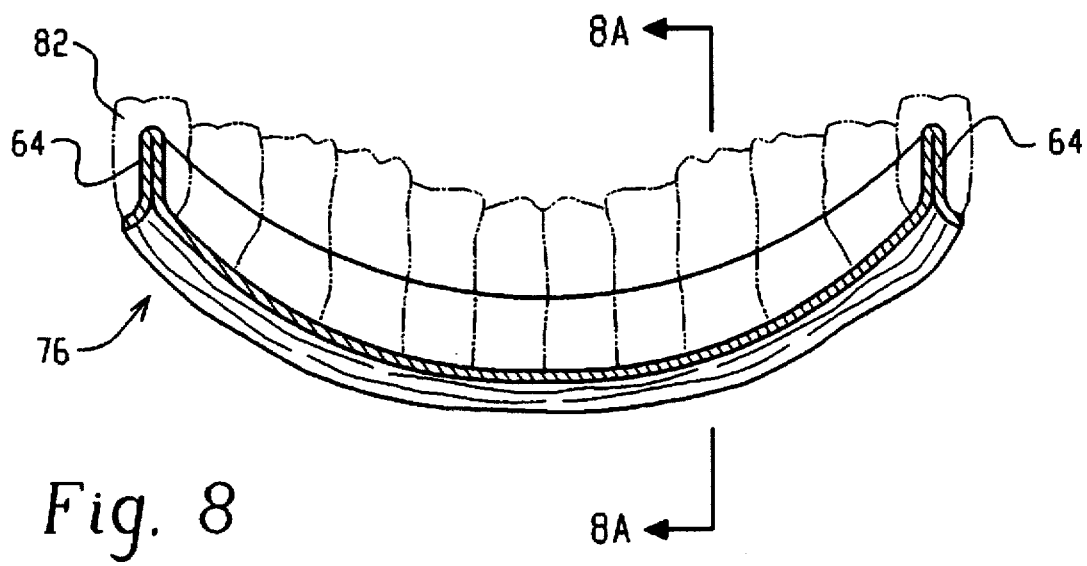
FIG. 8 is a cross-sectional view of a lower denture plate showing the location of teeth to be molded thereon; and, FIG. 8a is a cross sectional view taken along lines 8a—8a in FIG. 8.
Figure 8A:
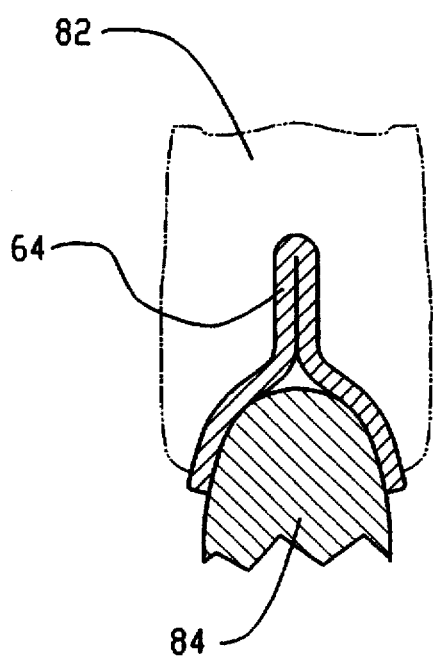

Referring now to FIG. 7, an outline for a full prosthetic denture is shown. As with the foregoing partial denture device, a prepreg 40 as discussed above is formed. According to the present invention, a strip 62 approximately one-inch-wide and approximately six-inches-long, is cut from a larger sheet of prepreg 40 at forty-five (45) degrees to the warp and fill fibers 60 of layer 42 forming sheet 40. The material may also be formed from a flat braid with the same fiber orientation. Strip 62 is creased along the center line and pinched to form a one-eighth-inch high rib 64. The base of rib 64 is stitched along lines 66, 68 according to conventional technology to hold rib 64 in position. Rib 64 is stitched to define an inside flap 72 and an outside flap 74. Strip 62 of prepreg 40 is then formed into a generally parabolic-shaped configuration, conforming to a center line of a patient's denture. In this respect, the forty-five degree orientation of warp and fill fibers 60 of layer 42 forming prepreg 40 allows for the forming of the parabolic shape without wrinkling or distorting prepreg 40. As with the partial denture appliance, the full denture appliance requires a plaster cast 10 of the patient's gum line. The parabolic shaped prepreg 40 is positioned over the parabolic shaped gum line of plaster cast 10, with one edge of prepreg 40 positioned on an inner wall of the gum line and the outer edge of prepreg 40 positioned on an outer wall of the gum line. Formed rib 64 is positioned on the top of the gum line along an axis conforming to the axis of the patient's normal teeth line. The inside and outside flaps 72, 74 are manually forced against the gum line, and rib 64 is positioned manually in the approximate position of the patient's teeth. According to the present invention, the strip of prepreg 40 is preferably vacuum formed onto the patient's gum line to form a smooth contour therewith. Preferably, thermosetting, light-curable, acrylic resin comprising rib 64 and prepreg 40 is light cured to form a rigid denture base 76, as seen in FIG. 8. With denture base 76 in position on plaster cast 10, artificial teeth 82 may be applied to rib 64. As indicated above, teeth 82 may be formed in a number of conventional ways. Preferably, according to the present invention, teeth 82 are formed to have slotted base portions, and the base portions are bonded to rib 64 formed on dental base 76 using known techniques. FIG. 8A shows a cross-sectional view of the denture base 76, as positioned on a patient's lower gums, as designated 84 in the drawing.

The present invention has been described with respect to preferred embodiments and a preferred method of forming same. Other alterations and modifications will occur to others skilled in the art upon their reading and understanding of this specification. It is intended that all such modifications and alterations fall within the scope of the invention as claimed and the equivalents thereof.

Having described the invention, the following is claimed:
1. A denture plate, comprising:
    a denture base formed of a composite laminate having an intermediate layer of fabric and having non-woven veils disposed on opposite sides thereof, said woven fabric and said non-woven veils encapsulated in a polymeric resin, said denture base molded to conform to a shape of a patient's mouth;

at least one tab extending from said denture base, said tab oriented to be in alignment with an orientation of a patient's natural teeth; and, a synthetic tooth molded on each tab.

2. The denture plate of claim 1, wherein said fabric is made of synthetic fibers.

3. The denture plate of claim 2, wherein said fabric is a woven fabric.

4. The denture plate of claim 3, wherein said synthetic fibers are made of polyethylene.

5. The denture plate of claim 4, wherein said non-woven veils are made of synthetic, acrylic based fibers.

6. The denture plate of claim 5, wherein said polymeric resin is a thermosetting resin.

7. The denture plate of claim 6 wherein said thermosetting resin is a light-curable, acrylic resin.

8. The denture plate of claim 2, wherein said fabric is comprised of cross-plied, unidirectional materials.

9. The denture plate of claim 1, wherein said fabric and said non-woven veils comprise at least about 50% to at least about 70% by weight of said denture plate, and said resin comprises at least about 50% to 30% by weight of said denture plate.

10. The denture plate of claim 1, wherein said fabric and said non-woven fabric comprise at least about 55% to at least about 65% by weight of said denture plate, and said resin comprises at least about 45% to at least about 35% by weight of said denture plate.

11. The denture plate of claim 1, wherein said fabric and said non-woven fabric comprise about 60% by weight of said denture plate, and said resin comprises about 40% of said denture plate.

12. The denture plate of claim 1, wherein said denture base has a thickness of up to about 0.060 inches.

13. A process for making a denture plate, comprising the steps of:

creating a cast of a patient's mouth, having a profile of the patient's palate and teeth formed thereon;

placing a prepreg laminate sheet onto said cast, said laminate sheet having an outer profile shaped to generally conform to and match said inner profile of said teeth;

tabs extending from said laminate sheets in registry with missing teeth of said cast, said tabs oriented to be in alignment with said teeth of said cast;

vacuum or pressure drawing said laminate onto said cast until said laminate conforms to said profile of said palate and said teeth;

curing said vacuum or pressure-drawn laminate sheet to form a rigid dental plate that conforms to said profile of said palate and teeth of the patient's mouth, wherein each of said tabs is oriented along a normal axis of the patient's teeth; and, molding an artificial tooth onto each tab.

14. A prosthetic denture device, comprising:

a dental base vacuum or pressure formed to conform to an interior surface of a patient's mouth, said dental base formed of resin impregnated, fiber reinforced laminate;

at least one tab extending from said dental base and oriented along a tooth axis relative to said denture base; and, an artificial tooth formed on each tab, said tooth to be in alignment with the natural position of the permanent teeth in a patient's mouth.

15. The denture plate of claim 14, wherein said resin is a thermoplastic.

16. The denture plate of claim 14, wherein said resin is a thermoset.

17. The denture plate of claim 14, wherein said laminate has a tensile modulus of at least about 0.75 million PSI.

18. A denture device, comprising:

a denture base formed of a composite laminate having an intermediate layer of a fabric and having non-woven veils disposed on each side thereof, said woven fabric and said non-woven veils encapsulated in a polymer, said denture base molded to conform to the shape of a patient's mouth;

at least one tab extending from said denture base, said tab oriented to be in alignment with the orientation of a patient's natural teeth;

a synthetic tooth molded on each tab; and, said composite laminate having a tensile modulus of at least about 0.75 million PSI.

19. The denture device of claim 18, wherein said fabric is a woven fabric.

20. The denture device of claim 18, wherein said fabric comprises cross-plied, unidirectional materials.

21. A full denture plate, comprising:

a dental base formed of a strip of a composite laminate having an intermediate layer of woven fabric, said fabric having warp and fill fibers, and having non-woven veils disposed on each side thereof, said woven fabric and said non-woven veils encapsulated in a polymeric resin, said strip cut from said laminate at about 45 degrees to said warp and fill fibers, said strip formed into a ridge having a base, said ridge generally conforming to a patient's gum line; and, synthetic teeth bonded to said ridge to form a complete set of dentures.

22. The denture plate of claim 21, wherein said woven fabric is made of synthetic fibers.

23. The denture plate of claim 22, wherein said synthetic fibers are made of polyethylene.

24. The denture plate of claim 23, wherein said non-woven veils are made of synthetic, acrylic based fibers.

25. The denture plate of claim 24, wherein said polymeric resin is a thermosetting resin.

26. The denture plate of claim 25, wherein said polymeric resin is a light-curable, acrylic resin.

27. The denture plate of claim 25, wherein said center woven material is a flat braid with ±45 degree fiber orientation.

28. A process for making a full denture plate, comprising the steps of:

creating a cast of a patient's gum line having an inner wall and an outer wall;

cutting a strip of prepreg, said prepreg made of fibers and a polymeric resin;

creasing along a center line and pinching said strip to form a rib and a base;

stitching said base to hold said rib in position; forming said strip into a generally parabolic shape having an inner edge and an outer edge;

placing said strip over said cast with said inner edge of said strip placed over said inner wall of said cast and said outer edge of said strip placed over said outer wall of said cast; said laminate strip being shaped to generally conform to and match the patient's gum line;

vacuum or pressure drawing said strip onto said cast;

curing said vacuum or pressure-drawn laminate strip to form a rigid dental base; and, molding a complete set of artificial teeth to said rib of said dental base.

29. The process of claim 28, wherein said laminate is comprised of an intermediate woven fabric having warp and fill fibers disposed between non-woven veils.

30. The process of claim 29, wherein said laminate strip is cut at an angle of about 45 degrees to said warp and fill fibers.

31. The process of claim 30, wherein said polymeric resin is a thermosetting polymer.

32. The process of claim 31, wherein said polymeric resin is a light-curable, acrylic resin.

33. The process of claim 28, wherein each artificial tooth has a base portion with a slot, said slot dimensioned to fit over said rib.

* * * * *